United States Patent
Mizuno et al.

(10) Patent No.: US 6,743,748 B2
(45) Date of Patent: Jun. 1, 2004

(54) CATALYST FOR PRODUCING EPOXY COMPOUNDS AND METHOD OF PRODUCING EPOXY COMPOUNDS USING THE SAME

(75) Inventors: Noritaka Mizuno, Tokyo (JP); Yasutaka Sumida, Neyagawa (JP); Koji Yonehara, Kyoto (JP); Masahiro Wada, Nishinomiya (JP); Minoru Urata, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/130,944

(22) PCT Filed: Mar. 6, 2002

(86) PCT No.: PCT/JP02/02056
§ 371 (c)(1),
(2), (4) Date: Mar. 7, 2003

(87) PCT Pub. No.: WO02/072257
PCT Pub. Date: Sep. 19, 2002

(65) Prior Publication Data
US 2003/0171604 A1 Sep. 11, 2003

(30) Foreign Application Priority Data
Mar. 12, 2001 (JP) .......................................... 2001-68819

(51) Int. Cl.[7] ................................................ B01J 21/14
(52) U.S. Cl. ........................ 502/254; 502/305; 549/524
(58) Field of Search ................................ 502/241, 242, 502/243, 248, 249, 253, 257, 262, 263, 305, 321; 549/523, 524

(56) References Cited

U.S. PATENT DOCUMENTS 5,681,973 A  10/1997  Hoelderich et al.

FOREIGN PATENT DOCUMENTS

| DE | 44 24 625 A1 | 1/1996 |
|----|--------------|--------|
| EP | 1 11 2 777 A1 | 7/2001 |
| JP | 5-237392 A | 9/1993 |
| JP | 2001-213871 A | 8/2001 |

*Primary Examiner*—Stanley S. Silverman
*Assistant Examiner*—Edward M. Johnson
(74) *Attorney, Agent, or Firm*—Sughrue Mion, PLLC

(57) ABSTRACT

The present invention provides a catalyst capable of producing an epoxy compound in high yield and improving the utilization efficiency of the oxidizing agent as well as a method of producing an epoxy compound using that catalyst.

A catalyst for producing an epoxy compound by oxidizing a compound having at least one ethylenic double bond with an oxidizing agent, comprising a polyatom-containing heteropolyoxometalate anion (A1) having two defective and/or three defective structure sites and containing silicon as the heteroatom, and an element (E1) being at least one element selected from the group consisting of vanadium, tantalum, niobium, antimony, bismuth, chromium, molybdenum, selenium, tellurium, rhenium, cobalt, nickel, ruthenium, rhodium, palladium, osmium, platinum, iridium, silver, gold, zinc, aluminum, gallium, indium, scandium, yttrium, titanium, zirconium, hafnium, germanium, tin and lanthanoids, and being different from the polyatom.

12 Claims, 1 Drawing Sheet

CATALYST FOR PRODUCING EPOXY COMPOUNDS AND METHOD OF PRODUCING EPOXY COMPOUNDS USING THE SAME

BACKGROUND OF THE INVENTION

The present invention relates to a catalyst for producing an epoxy compound and a method of producing an epoxy compound using the same. More particularly, it relates to a catalyst for producing an epoxy compound by catalytically oxidizing a compound having at least one ethylenic double bond with an oxidizing agent and to a method of producing an epoxy compound using said catalyst.

PRIOR ART

Epoxy compounds (epoxides) are compounds useful as intermediates or raw materials for the production of various industrial products. As actual examples of the production of industrial products using epoxy compounds as intermediates, there may be mentioned the conversion of ethylene oxide into ethylene glycol or polyethylene glycol, and the formation of polyether polyols such as polypropylene polyethers by alkoxylation of alcohols with propylene oxide. The thus-produced industrial products are consumed in large amounts in the production of polyurethanes and synthetic elastomers.

Epoxy compounds also serve as important intermediates for the production of alkylene glycols, such as propylene glycol and dipropylene glycol, and alkanolamines, which are among important industrial products as raw materials of solvents and surfactants.

As a method of synthesizing epoxy compounds, there may be mentioned, the epoxidation reaction of compounds having an ethylenic double bond, for example olefins, and this is one of commercially important chemical conversion methods. In this synthetic method, epoxy compounds are synthesized by adding one oxygen atom to the carbon—carbon double bond and, for producing ethylene oxide from ethylene, for instance, the method using a silver catalyst is well known and, for producing propylene oxide from propylene, the chlorohydrin method or the Halcon process using an organic hydroperoxide is well known. These methods have been put to practical use on commercially. However, the chlorohydrin method, for instance, has the problem of generation of a low concentration hydrogen chloride vapor.

In such epoxidation reaction, an olefin is converted to an epoxy compound using hydrogen peroxide as an oxidizing agent, and the use, as catalysts, of heteropolyoxometalates having a structure such that there is a heteroatom at the center with polyatoms coordinated to the heteroatom each via an oxygen atom is now studied. As for heteropolyoxometalates which are used as catalysts, it is known that ones having a defectivee structure lacking in an atom or atoms which should normally occur in the crystal structure and containing a metal element, namely ones resulting from substitution of polyatom with other metal element show catalytic activity.

Regarding such metal-containing heteropolyoxometalates, the following studies are carried out.

As an example of the use of one defective type heteropolyoxometalates as catalysts, J. Mol. Catal., A: Chemical, 108 (1996), p. 135–143 discloses an example of epoxidation of cyclohexene with hydrogen peroxide in the presence of a Cr-substituted one defective Keggin-structure heteropolytungstate $[PW_{11}O_{39}]^{7-}$ catalyst, and J. Mol. Catal., A: Chemical, 117 (1997), p. 389–396 discloses a method of synthesizing the epoxide from cyclohexene and hydrogen peroxide using Fe(III), Cr(III), Ru(IV), Ti(IV) and V(IV) complexes of one defective type $[PW_{11}O_{39}]^{7-}$ as catalysts. However, even when these catalysts are used, the epoxide namely epoxycyclohexane yield was low.

As an example of the use of two defective type heteropolyoxometalates as catalysts, there is the following disclosure. Thus, J. Catal., 182 (1999), p. 285–288 discloses an example of the epoxidation reaction of olefins such as cyclooctene and 2-octene with hydrogen peroxide using, as catalysts, two defective Keggin-structure silicotungstate species respectively substituted by the cations Fe, Mn and Cu. However, in spite of the olefin being cyclooctene, the catalytic activities are low. In particular when the proportion of hydrogen peroxide relative to the olefin becomes high, the utilization efficiency of hydrogen peroxide decreases markedly.

J. Am. Chem. Soc., 117, p. 681 discloses Ti- or V-substituted two defective type catalysts $K_7[PTi_2W_{10}O_{40}]$ and $H_5[PV_2Mo_{10}O_{39}]$. However, in the reactions using such Ti- or V-substituted catalysts containing phosphorus as the heteroatom, the epoxidation activity was very low.

J. Mol. Catal., A: Chemical, 114 (1996), p. 237–245, and 142 (1999), p. 61–76 respectively disclose a method of epoxidizing cyclooctene with hydrogen peroxide using Ti-substituted one defective and two defective type heteropolyacids $[PTiW_{11}O_{40}]^{5-}$ and $[PTi_2W_{10}O_{40}]^{7-}$ catalysts. However, the productivity of the epoxide was low.

Further, as an example of the use of lanthanoid-containing defective type heteropolyoxometalates as catalysts, Bull. Chem. Soc. Jpn, 66 (1993), p. 2790–2796 discloses a heteropolytungstolanthanate anion catalyst represented by $(M(Ce,Nd,Sm)W_{10}O_{36};LnW_{10})$. In this case, the anion has the Weakley structure, and the lanthanoids(III) are coordinated to the polyacid $W_5O_{18}$. However, there is no olefin oxidation example.

Kidorui, 30 (1997), p. 288–289 discloses an epoxidation reaction of allyl alcohols by oxidation with hydrogen peroxide using a Weakley-structure heteropolyacid containing rare earth elements with lanthanoid elements(III) as core elements. The structure of this polyacid is not the so-called Keggin structure. Further, Kidorui, 16 (1990), p. 46–47 discloses the synthesis of a tetravalent terbium-substituted one defective type heteropolyacid $[PW_{11}O_{39}]^{7-}$.

Polyhedron, 15 (1996), p. 3493–3500 discloses an example of the epoxidation reaction of cyclooctene with hydrogen peroxide using, as catalysts, lanthanoid-containing Weakley-structure heteropolyacids, namely $[LnW_{10}O_{36}]^{9-}$ and $[Ln\{PW_{11}O_{39}\}_2]^{11-}$, or lanthanoid polyoxotungstate. The productivity of the epoxide is fairly high. However, there is no disclosure concerning polyoxometallates having the two defective type Keggin structure.

Indian J. Chem., 37A (1998), p. 816–819 discloses a Ln(La,Pr,Nd,Sm,Gd) metal-substituted one defective Keggin-structure heteropolyacid, $[Ln(PW_{11}O_{39})_2]$. However, there is no olefin epoxidation example.

Radiochemistry, 41 (1999), p. 1–23 discloses one defective type Keggin-structure and one defective Dawson-structure polyoxometallates as lanthanoid polyoxometallates. However, there is no example disclosed of the two defective type.

In the above study examples, the investigations concerning the application of heteropolyoxometalates to the epoxidation reaction remain insufficient. Thus, when heteropolyoxometalates are applied to the epoxidation reaction, their catalytic activity and the utilization efficiency of the oxidizing agent are insufficient, so that there is room for contrivance for rendering them suited as catalysts for the epoxidation reaction of olefins and the like, which is a method of producing commercially important epoxy compounds.

SUMMARY OF THE INVENTION

It is an object of the present invention, which has been made in view of the above-mentioned state of the art, to provide a catalyst capable of producing an epoxy compound in high yield and improving the utilization efficiency of the oxidizing agent on the occasion of catalytically oxidizing a compound having at least one ethylenic double bond with an oxidizing agent such as hydrogen peroxide to produce the corresponding epoxy compound, as well as a method of producing an epoxy compound using that catalyst.

The present inventors made various investigations in search of catalysts for producing an epoxy compound by oxidizing a compound having at least one ethylenic double bond with an oxidizing agent and, as a result, noticed that heteropolyoxometalates are useful commercially and found that (1) a catalyst which comprising a polyatom-containing heteropolyoxometalate anion (A1) having two defective and/or three defective structure sites and containing a silicon atom as a heteroatom, and a specific element (E1), (2) a catalyst which comprising a heteropolyoxometalate anion (A2) containing phosphorus as a heteroatom and molybdenum and/or tungsten as a polyatom and having two defective and/or three defective structure sites, and a specific element (E2), and (3) a catalyst which comprising a heteropolyoxometalate anion (A3) containing phosphorus as a heteroatom and tungsten as a polyatom and having two defective and/or three defective structure sites, and a specific element (E3) are suited for use in the above oxidation reaction to produce an epoxy compound in high yield while improving the utilization efficiency of the oxidizing agent. They also found that such heteropolyoxometalate anions, when they are Keggin-structure heteropolyoxometalate anions having a specific structure, can produce their effects as catalysts in the above epoxidation reaction to more satisfactory extent. So, they have now completed the present invention.

Thus, the present invention provides a catalyst for producing an epoxy compound by oxidizing a compound having at least one ethylenic double bond with an oxidizing agent, which comprises a polyatom-containing heteropolyoxometalate anion (A1) having two defective and/or three defective structure sites and containing silicon as a heteroatom, and an element (E1) being at least one element selected from the group consisting of vanadium, tantalum, niobium, antimony, bismuth, chromium, molybdenum, selenium, tellurium, rhenium, cobalt, nickel, ruthenium, rhodium, palladium, osmium, platinum, iridium, silver, gold, zinc, aluminum, gallium, indium, scandium, yttrium, titanium, zirconium, hafnium, germanium, tin and lanthanoids, and being different from the polyatom.

The invention also provides a catalyst for producing an epoxy compound by oxidizing a compound having at least one ethylenic double bond with an oxidizing agent, which comprises a heteropolyoxometalate-anion (A2) containing phosphorus as a heteroatom and molybdenum and/or tungsten as a polyatom and having two defective and/or three defective structure sites and an element (E2) being at least one element selected from the group consisting of elements of the fourth to sixth periods of group IIIa, elements of the fourth to sixth periods of groups VIa to VIII, elements of the fourth to sixth periods of groups Ib to IIb, elements of the third to sixth periods of group IIIb, and elements of the fourth to sixth periods of groups IVb to Vb of the periodic table, and being different from the polyatom.

The present invention further provides a catalyst for producing an epoxy compound by oxidizing a compound having at least one ethylenic double bond with an oxidizing agent, which comprises a heteropolyoxometalate anion (A3) containing phosphorus as a heteroatom and tungsten as a polyatom and having two defective and/or three defective structure sites, and an element (E3) being at least one element selected from the group consisting of elements of the fourth to sixth periods of group Va.

The invention is also directed to a method of producing an epoxy compound by oxidizing a compound having at least one ethylenic double bond with an oxidizing agent, wherein said method of producing the epoxy compound comprises using one of the above-mentioned catalysts.

In the following, the present invention is described in detail.

DETAILED DESCRIPTION OF THE INVENTION

Figure 1:
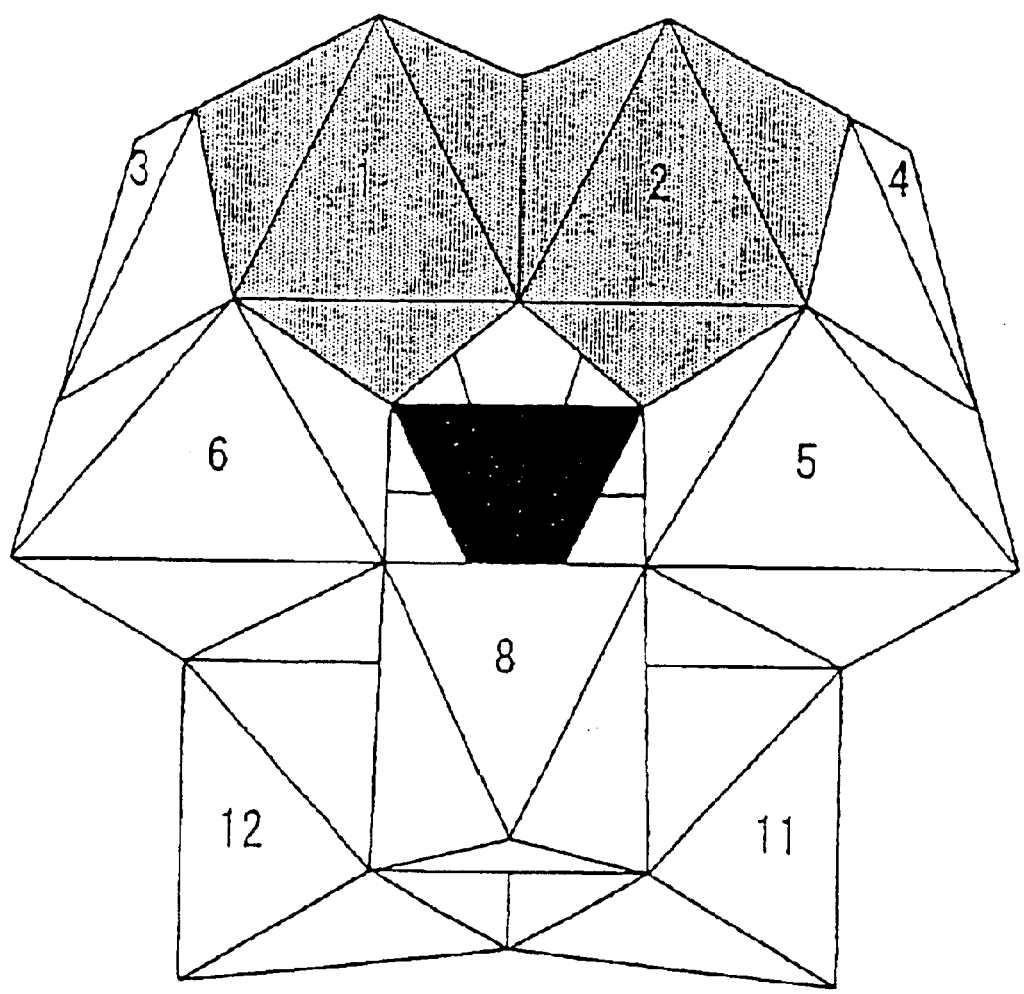
FIG. 1 is a schematic representation of the molecular structure of a vanadium-substituted polyoxometallate, $[\gamma\text{-SiW}_{10}\{V\}_2O_{38}]$ or $[\gamma\text{-PW}_{10}\{V\}_2O_{40}]$. Each shaded octahedron represents a V. Each white octahedron represents a $WO_6$ octahedron. The central black tetrahedron represents $SiO_2$ in the case of $[\gamma\text{-SiW}_{10}\{V\}_2O_{38}]$ or $PO_4$ in the case of $[\gamma\text{-PW}_{10}\{V\}_2O_{40}]$. In the figure, each number represents n of Wn, and Wn is the number of $WO_6$ in the Keggin structure according to the IUPAC nomenclature.

The catalyst of the invention is used for producing an epoxy compound by oxidizing a compound having at least one ethylenic double bond with an oxidizing agent and has (1) the form which comprises a polyatom-containing heteropolyoxometalate anion (A1) having two defective and/or three defective structure sites and containing a silicon atom as a heteroatom, and an element (E1), (2) the form which comprises a heteropolyoxometalate anion (A2) containing phosphorus as a heteroatom and molybdenum and/or tungsten as a polyatom and having two defective and/or three defective structure sites, and an element (E2), or (3) the form which comprises a heteropolyoxometalate anion (A3) containing phosphorus as a heteroatom and tungsten as a polyatom and having two defective and/or three defective structure sites, and an element (E3). Thus, such catalyst comprises a heteropolyoxometalate anion having two defective structure sites lacking in two polyatoms which should normally occur in the crystal structure and/or a heteropolyoxometalate anion having three defective structure sites lacking in three polyatoms and an element being different from the polyatom, and may comprise one single species or two or more species. An appropriate combination of the three forms of catalysts (1) to (3) may also be used. Such catalysts produce, in the main, the following effects (1) to (8).

Thus, the following may be mentioned: (1) isomerization reactions leading to the formation of aldehydes or ketones, hardly occur, so that the selectivity toward epoxy compounds increases; (2) glycol monoalkyl ethers and the like, which are formed by the reaction of glycols formed upon water-induced ring opening of epoxy compounds, namely the desired products, with compounds having at least one ethylenic double bond as reactant substrates are formed only in small amounts and this also leads to very high levels of selectivity toward the epoxy compounds; (3) even when water or an alcohol is present in large amounts in the reaction system, such side reactions as isomerization and ring opening reactions hardly occur and, accordingly, the selectivity toward epoxy compounds increases, so that an oxidizing agent, such as hydrogen peroxide, can be used at a low concentration; (4) in cases where the oxidizing agent is hydrogen peroxide, the decomposition thereof to oxygen occurs only to a small extent and the utilization efficiency of the oxidizing agent in forming epoxy compounds increases; (5) even when hydrogen peroxide is used in a low proportion relative to the reactant substrate compounds having at least one ethylenic double bond, the reaction activity is high and the selectivity is improved; (6) the catalysts have high activity; (7) byproduct ketones, such as acetone, are formed only in small amounts and, organic peroxides are hardly formed from acetone, whereby the danger of explosion or like hazards is rendered low; (8) the consumption of the oxidizing agent, such as hydrogen peroxide, due to accumulation of organic peroxides during the reaction process is little.

In the above form (1) of catalyst, the polyatom-containing heteropolyoxometalate anion having two defective and/or three defective structure sites and containing silicon as the heteroatom has a crystal structure such that 10 or 9 polyatoms are coordinated, each via an oxygen atom, to the silicon atom which is the heteroatom, and may comprise one single species or two or more species. Suited as the polyatoms are molybdenum, tungsten, vanadium, niobium and like atoms. Thus, the above polyatom-containing heteropolyoxometalate anion having two defective and/or three defective structure sites and containing silicon as the heteroatom is preferably a Keggin-structure heteropolyoxometalate anion represented by the following general formula (1):

$$[SiM_{10}O_{36}]^{q-} \quad (1)$$

and/or the following general formula (2):

$$[SiM_9O_{34}]^{q-} \quad (2)$$

in the formulas (1) and (2), Si represents a silicon atom, Ms are the same or different and each represents at least one element selected from the group consisting of molybdenum, tungsten, vanadium and niobium and q is a positive integer. The number q is determined by the valence of the element M.

The element (E1), which is one of the essential component of the above catalyst, is different from the polyatom and at least one element selected from the group consisting of vanadium, tantalum, niobium, antimony, bismuth, chromium, molybdenum, selenium, tellurium, rhenium, cobalt, nickel, ruthenium, rhodium, palladium, osmium, platinum, iridium, silver, gold, zinc, aluminum, gallium, indium, scandium, yttrium, titanium, zirconium, hafnium, germanium, tin and lanthanoids. Preferred among them are V, Sb, Mo, Cr, Re, Co, Ni, Ru, Pd, Au, Zn, Y, Sn and lanthanoids. More preferred are V, Mo, Pd, Ru, Au, Zn, Y and lanthanoids.

The content of element (E1) in the catalyst of the invention is preferably above 0 (zero), more preferably not less than 0.0001 atom, still more preferably not less than 0.01 atom, per Si atom in the catalyst. On the other hand, it is preferably not more than 6 atoms, more preferably not more than 5 atoms, still more preferably not more than 3 atoms.

In the above form (2) or (3) of catalyst, the heteropolyoxometalate anion (A2) containing phosphorus as the heteroatom and molybdenum and/or tungsten as the polyatom and having two defective and/or three defective structure sites or the heteropolyoxometalate anion (A3) containing phosphorus as the heteroatom and tungsten as the polyatom and having two defective and/or three defective structure sites has a crystal structure such that 10 or 9 polyatoms are coordinated, each via an oxygen atom, to the phosphorus atom which is the heteroatom, and may comprise one single species or two or more species.

In the above form (2) or (3) of catalyst, the above heteropolyoxometalate anion having two defective and/or three defective structure sites is preferably a Keggin-structure heteropolyoxometalate anion. Thus, the heteropolyoxometalate anion (A2) having two defective and/or three defective structure sites is preferably a Keggin-structure heteropolyoxometalate anion represented by the following general formula (3):

$$[P_1M_{10}O_{36}]^{q-} \quad (3)$$

and/or the following general formula (4):

$$[P_1M_9O_{34}]^{q-}$$

in the formulas (3) and (4), P represents a phosphorus atom, Ms are the same or different and each represents molybdenum or tungsten and q is a positive integer. The number q is determined by the valence of the element M. The above-mentioned heteropolyoxometalate anion (A3) having two defective and/or three defective structure sites is preferably a Keggin-structure heteropolyoxometalate anion represented by the following general formula (5):

$$[P_1W_{10}O_{36}]^{7-} \quad (5)$$

and/or the following general formula (6):

$$[P_1W_9O_{34}]^{9-} \quad (6)$$

in the formulas (5) and (6), P represents a phosphorus atom and W represents a tungsten atom.

The element (E2), which is an essential component of the above form (2) of catalyst, is an element different from the polyatom and at least one element selected from the group consisting of elements of the fourth to sixth periods of group IIIa, elements of the fourth to sixth periods of groups VIa to VIII, elements of the fourth to sixth periods of groups Ib to IIb, elements of the third to sixth periods of group IIIb, and elements of the fourth to sixth periods of groups IVb to Vb of the periodic table. Preferred among these are Cr, Mo, Mn, Re, Fe, Co, Ni, Ru, Rh, Pd, Os, Ir, Pt, Cu, Au, Zn, Al, In, Ge, Sn, Sb, Bi, Sc, Y and lanthanoid elements. More preferred are Mo, Re, Rh, Ir, Zn and lanthanoid elements. Still more preferred are Zn, Re, Mo and Rh. "An element different from the polyatom" means that when the polyatoms are molybdenum and/or tungsten, that element is an element other than molybdenum and/or tungsten but among the elements mentioned above.

The element (E3), which is an essential component of the above form (3) of catalyst, is at least one element selected from the group consisting of the elements of the fourth to sixth periods of group Va, namely the elements V, Nb and Ta. Among them, V is preferred, however.

The content of the element (E2) or element (E3) in the catalyst of the invention is preferably above 0 (zero), more preferably not less than 0.0001 atom, still more preferably not less than 0.01 atom, per phosphorus atom in the catalyst. On the other hand, it is preferably not more than 6 atoms, more preferably not more than 5 atoms, still more preferably not more than 3 atoms.

The element (E1), (E2) or (E3) in the above catalyst may have the form of a cation to keep a balance with the charge of the heteropolyoxometalate anion or may have the form of an oxide.

As for the form of occurrence of the element (E1), (E2) or (E3) (hereinafter collectively referred to also as the element (E)) and of the heteropolyoxometalate anion (A1) or heteropolyoxometalate anion (A2) or (A3) (hereinafter collectively referred to also as the heteropolyoxometalate anion (A)), it is only required that the heteropolyoxometalate anion (A) and the element (E) be coexisting in the catalyst. For example, the following forms of bonding (1) to (3) are preferred.

(1) The form in which the element (E) occur as substituents in the two defective and/or three defective sites of the heteropolyoxometalate anion (A). In this case, the respective elements (E) are preferably adjacent to each other. Available as isomers in which the respective elements (E) are adjacent to each other are the $\alpha$, $\beta$, $\gamma$, $\delta$, $\epsilon$ and like forms. The isomers $\alpha$ and $\beta$ are corner-sharing isomers. More preferred are the $\gamma$, $\delta$ and $\epsilon$ forms in which two elements (E) are incorporated, in an edge-sharing manner, in the skeleton of a two defective Keggin-structure heteropolyoxometalate anion. Among them, the $\gamma$ form is most preferred. The $\gamma$ form can be prepared, for example, by the method described in Inorganic Syntheses, vol. 27, p. 85–96I or J. Am. Chem. Soc., 120, p. 9267. As an example of the $\gamma$ form, the $[\gamma\text{-SiW}_{10}\{V\}_2O_{38}]^{q-}$ or $[\gamma\text{-PW}_{10}\{V\}_2O_{40}]^{q-}$ anion is illustrated in FIG. 1. The elements V are shown in a condition such that they occupy two $WO_6$ portions (two defective sites) each originally having an octahedral structure and occur adjacent to each other and in an edge-sharing manner.

(2) The form in which the element (E) occur in a state coordinated with a heteropolyoxometalate anion or anions having two defective or three defective sites, for example in the manner of $\{SiM_{10}O34\}^{q-}\text{-E-O-E-}\{SiM_{10}O_{34}\}^{q-}$ or $\{SiM_{10}O_{34}\}^{q-}\text{-E-}\{SiM_{10}O_{34}\}^{q-}$ or in the manner of $\{PM_{10}O_{36}\}^{q-}\text{-E-O-E-}\{PM_{10}O_{36}\}^{q-}$ or $\{PM_{10}O_{36}\}^{q-}\text{-E-}\{PM_{10}O_{36}\}^{q-}$.

In the above form (1) or (2), the structure resulting from bonding of the element (E) and the heteropolyoxometalate anion (A) can be determined or estimated by X ray analysis, elemental analysis and FT-IR spectrometry.

(3) The form in which the element (E) is carried or adsorbed on the heteropolyoxometalate anion (A) having two defective and/or three defective sites. In this case, the sites where the element (E) is carried or adsorbed in the heteropolyoxometalate anion (A) are not particularly restricted. Such a form can be estimated by elemental analysis and FT-IR and so on.

Said heteropolyoxometalate anion having two defective or three defective sites may form a salt. Suitable as the cation to form a salt with the heteropolyoxometalate anion are, for example, proton, alkali metal cations (lithium ions, sodium ions, potassium ions, rubidium ions, cesium ions), alkaline earth metal cations (beryllium ions, magnesium ions, calcium ions, strontium ions, barium ions), and organic cation-containing cations such as quaternary ammonium salts (e.g. tetramethylammonium salt, tetraethylammonium salt, tetrapropylammonium salt, tetrabutylammonium salt, tributylmethylammonium salt, trioctylmethylammonium salt, trilaurylmethylammonium salt, benzyltrimethylammonium salt, benzyltriethylammonium salt, benzyltributylammonium salt), quaternary phosphonium salts (e.g. tetramethylphosphonium salt, tetraethylphosphonium salt, tetrapropylphosphonium salt, tetrabutylphosphonium salt, tetraphenylphosphonium salt, ethyltriphenylphosphonium salt, benzyltriphenylphosphonium salt), quaternary arsoniums, and cetylpyridinium salts. The cation may comprise one single species or two or more species.

The amount of the catalyst of the invention to be used is preferably, for example, not less than 100,000/1, more preferably not less than 10,000/1 but preferably not more than 1/10, more preferably not more than 1/1 as expressed in terms of the mole ratio relative to the ethylenic double bond in the reactant substrate, namely the compound having at least one ethylenic double bond (number of moles of the ethylenic double bond in the reactant substrate/number of moles of the heteropolyoxometalate anion (A) having two defective and/or three defective structure sites).

Although the catalyst of invention preferably comprises, as essential components and as main components, (1) the polyatom-containing heteropolyoxometalate anion (A1) having two defective and/or three defective structure sites and containing silicon as the heteroatom and the element (E1), (2) the heteropolyoxometalate anion (A2) containing phosphorus as the heteroatom and molybdenum and/or tungsten as the polyatoms and having two defective and/or three defective structure sites and the element (E2), or (3) the heteropolyoxometalate anion (A3) containing phosphorus as the heteroatom and tungsten as the polyatoms and having two defective and/or three defective structure sites and the element (E3), or a mixture of these, as mentioned above, the catalyst may contain an impurity formed in the process of catalyst preparation and/or another component as long as the effects of the present invention are produced.

The catalyst of the present invention is suitably used for the method of producing an epoxy compound by oxidizing a compound having at least one ethylenic double bond with an oxidizing agent and is capable of producing an epoxy compound in high yield and improving the utilization efficiency of the oxidizing agent. Such a method of producing an epoxy compound using the catalyst of the invention is comprised in the present invention.

In the following, the reaction substrate, oxidizing agent, production conditions and other conditions to be used in the method of producing an epoxy compound according to the present invention are mentioned.

The reactant substrate to be used in the invention, namely the compound having at least one ethylenic double bond, may be an acyclic or cyclic organic compound and may comprise one or more of hydrocarbons, esters, alcohols, ethers, and halo-substituted hydrocarbons, for instance. Specifically, there may be mentioned straight-chain alkenes having a terminal ethylenic double bond, such as ethylene, propylene, 1-butene, butadienes, 1-hexene, 1-pentene, isoprene, diisobutylene, 1-heptene, 1-octene, 1-nonene, 1-undecene, 1-dodecene, 1-tridecene, 1-tetradecene, 1-pentadecene, 1-heptadecene, 1-octadecene, 1-nonadecene, 1-eicocene propylene trimer and tetramers, and 1,3-butadiene; alkenes or branched alkenes having an ethylenic double bond in the molecule, such as 2-butene, 2-octene, 2-methyl-2-hexene, and 2,3-dimethyl-2-butene; and alicyclic olefinic hydrocarbons such as cyclopentene, cyclohexene, 1-phenyl-1-cyclohexene, 1-methyl-1-cyclohexene, cycloheptene, cyclooctene, cyclodecene, cyclopentadiene, cyclodecatriene, cyclooctadiene, dicyclopentadiene, methylenecylopropane, methylenecyclopentane, methylenecyclohexane, vinylcyclohexane, cyclooctene and norbornene, among others. Among these, unsaturated hydrocarbons containing 2 to 15 carbon atoms are preferred. More preferred are unsaturated hydrocarbons containing 2 to 12 carbon atoms.

The compound having at least one ethylenic double bond may also have such a group as —COOH, —CN, —COOR or —OR (R being an alkyl, cycloalkyl, aryl or allylalkyl substituent), or an aryl, allylalkyl, halogen, nitro, sulfo, carbonyl (e.g. ketone or aldehyde), hydroxyl or ether group. As such compound, there may be mentioned, among others, allyl alcohol, allyl chloride, allyl methyl ether, allyl vinyl ether, diallyl ether, allyl phenyl ether, methyl methacrylate, acrylic acid and the like.

Also usable as the above compound having at least one ethylenic double bond are carbon—carbon double bond-containing aryl compounds containing 6 or more carbon atoms. As such compounds, there may be mentioned, among others, styrene, substituted styrenes such as a-methylstyrene, divinylbenzenes, stilbene, aralkenes; carbon—carbon double bond-containing amines, thiols, sulfides, disulfides, Se-, Te-, Sb or As-containing compounds, phosphines and phosphites.

The oxidizing agent to be used in the invention may be one capable of generating an oxygen ion or radical, a peroxide, or a superperoxide, for instance. Suited for use are, for example, hydrogen peroxide, tert-butyl peroxide, organic peroxides such as peracetic acid, oxygen-hydrogen mixed gases, dinitrogen monoxide, iodosylbenzene and the like. Among them, hydrogen peroxide is preferably used.

Hydrogen peroxide is an ideal oxidizing agent if the desired reaction proceeds selectively. In the prior art, however, the water formed in the reaction system may cause ring opening of the product epoxy compound, hence a decrease in yield, or the cost of hydrogen peroxide may become relatively high when the price of the product epoxy compound is low. So, the cost of production may become high. In the present invention, these problems are solved because of a high selectivity for the epoxy compound, high utilization efficiency of hydrogen peroxide and high productivity of epoxy compound with the catalyst.

When hydrogen peroxide is used as the oxidizing agent in the method of producing epoxy compounds according to the present invention, hydrogen peroxide is preferably used, in the form of a solution in water or alcohols at a concentration of 0.01 to 70% by mass, although 100% hydrogen peroxide can also be used. The catalyst to be used in the present invention is characterized in that even when hydrogen peroxide is used in a very low concentration, byproducts are hardly formed.

The amount of the above oxidizing agent to be used is preferably not less than 100/1, more preferably not less than 10/1, but preferably not more than 1/100, more preferably not more than 1/50, as expressed in terms of mole ratio relative to the ethylenic double bond in the reactant substrate, namely the compound having at least one ethylenic double bond (number of moles of the ethylenic double bond in the reactant substrate/number of moles of the oxidizing agent).

As for the reaction method in the production method of the invention, the epoxidation reaction is preferably carried out by catalytic oxidation. From the reaction activity viewpoint, the reaction is preferably carried out in a homogeneous liquid phase system by dissolving the catalyst, the compound having at least one ethylenic double bond, and the oxidizing agent in a solvent.

As the solvent mentioned above, water and/or an organic solvent is used. The organic solvent may comprise one single species or two or more species. Preferred are those which will not react with the compound having at least one ethylenic double bond which is the reactant substrate, the oxidizing agent such as hydrogen peroxide, or the product epoxy compound. As such organic solvent, there may be mentioned, among others, primary, secondary or tertiary monohydric alcohols containing 1 to 6 carbon atoms, such as methanol, ethanol, normal- or isopropanol and tert-butanol; polyhydric alcohols such as ethylene glycol, propylene glycol and glycerol; oligomers resulting from ring opening of ethylene oxide or propylene oxide, such as diethylene glycol and triethylene glycol; ethers such as ethyl ether, isopropyl ether, dioxane and tetrahydrofuran; esters such as ethyl acetate and formic acid esters or acetic acid esters of polyhydric alcohols; ketones such as acetone, methyl ethyl ketone, methyl isobutyl ketone and acetylacetone; nitrogen compounds such as dimethylformamide, nitromethane and nitriles; phosphorus compounds, for example phosphate esters such as triethyl phosphate and diethyl hexyl phosphates; halogenated hydrocarbons such as chloroform, dichloromethane and ethylene dichloride; aliphatic hydrocarbons such as n-hexane and n-heptane; aromatic hydrocarbons such as toluene and xylene; and alicyclic hydrocarbons such as cyclohexane and cyclopentane.

Preferably used among the solvents mentioned above are water, alcohols containing 1 to 4 carbon atoms, 1,2-dichloroethane, heptane, toluene, xylene, chlorobenzene, acetonitrile, benzonitrile, dimethyl sulfoxide, dimethylformamide and the like, and a mixture of these. In cases where water is present, it is also possible to allow a phase transfer catalyst and/or a surfactant to coexistence as the case may be.

As for the reaction method in the production method of the invention, the epoxidation reaction can be carried out by suspending the catalyst in the liquid phase without dissolving the same in a solvent. It is also possible to carry out the reaction in the so-called heterogeneous reaction system using the catalyst as a solid phase and the reactants, such as the reactant substrate and oxidizing agent, as a gaseous phase. In this case, the reaction is preferably carried out by carrying the catalyst on a carrier, or using the catalyst itself as a solid, and adding the reactants thereto. Usable as the carrier for the catalyst are those generally used in catalytic reactions in heterogeneous systems, such as various ion exchange resins, silica, alumina and other oxides.

In the above epoxidation reaction, it is preferred that the reaction system be neutral to acidic. Although, in the invention, the reaction system can be rendered acidic by using the above catalyst, an acidic substance may further be added to the reaction system. The acidic substance may be a Brønsted acid or a Lewis acid, for instance, and may comprise one single species or two or more species. Suitable as the Bronsted acid are, for example, mineral acids such as hydrochloric acid, sulfuric acid, nitric acid, phosphoric acid and boric acid; organic acids such as acetic acid, benzoic acid, formic acid, trichloroacetic acid, trifluoromethanesulfonic acid and sulfonic acid; zeolites, mixed oxides and like inorganic acids. Suitable as the Lewis acid are aluminum chloride, ferric chloride, boron chloride compounds, antimony chloride compounds, stannic chloride, antimony fluoride, zinc compounds, titanium compounds, zeolites, mixed oxides and the like. Furthermore, inorganic or organic acidic salts may also be used.

As for the reaction conditions in the above epoxidation reaction, the temperature, for instance, is preferably not lower than 0° C., more preferably not lower than room temperature, but preferably not higher than 250° C., more preferably not higher than 180° C. The reaction time is preferably not shorter than several minutes but not longer than 150 hours, more preferably not longer than 48 hours. The reaction pressure is preferably not lower than ordinary pressure but not higher than $2 \times 10^7$ Pa, more preferably not higher than $5 \times 10^6$ Pa. It is also possible to carry out the reaction under reduced pressure.

By using the above catalyst, the method of producing an epoxy compound according to the present invention is a method by which an epoxy compound is produced in high yield and is improved the utilization efficiency of an oxidizing agent. Thus, it can suitably be applied as a production method for providing epoxy compounds which are useful as intermediates or raw materials to be used in the production of various commercial products. Among the epoxy compounds obtainable by the production method of the present invention, ethylene oxide, which can serve as the raw material for ethylene glycol or polyethylene glycol, and propylene oxide, which can serve as the raw material for the production of polyether polyols, are commercially important. These epoxy compounds are also important intermediates for the production of alkylene glycols such as propylene glycol and dipropylene glycol, and alkanolamines, which are important industrial products as raw materials for solvents and surfactants.

DESCRIPTION OF PREFERRED EMBODIMENTS

The following examples illustrate the present invention in more detail. These examples are, however, by no means limitative of the scope of the present invention. Unless otherwise specified, "part(s)" means "part(s) by weight".
(1) Catalyst Preparation (Hereinafter the Catalyst Name is Given in Terms of Element Name-POM, for Instance)
V-POM (Preparation of V-Substituted Two Defective Type Heteropolyacid)

Two defective Keggin-structure $K_8[\gamma\text{-SiW}_{10}O_{36}] \cdot 12H_2O$ (10 g) prepared by the method described in Inorganic Syntheses, vol. 27, p. 88 was dissolved in 30 ml of a 1 mol/l aqueous solution of HCl at room temperature, and 13.5 ml of a 0.5 mol/l aqueous solution of $NaVO_3$ was added to the solution. After 5 minutes of stirring, the insoluble materials were filtered off. To the filtrate were added 8.84 g of tetrabutylammonium bromide and 40 g of deionized water, and stirring was continued for 20 minutes, followed by filtration. The recovered solid was dried at room temperature for 3 hours. This recovered solid was dissolved in 40 ml of acetonitrile, then 400 ml of deionized water was gradually added, and the mixture was stirred for 10 minutes while cooling with ice water at 0° C. Thereafter, the solid was recovered by filtration and dried at room temperature for 3 hours. This procedure comprising washing with acetonitrile and deionized water, filtration and drying was repeated once more to give a catalyst (V-POM).

V-POM (0.11 g) was dissolved in 0.35 ml of acetonitrile, and 0.11 g of silica (product of Fuji Silysia Chemical, trademark: "CARiACT Q-15") was added thereto. After stirring, the acetonitrile was distilled off using an evaporator while heating the mixture, the residue was washed with water several times to give 0.21 g of a carried catalyst (V-POM/SiO$_2$).
Fe-POM Catalyst (Preparation of Fe-Substituted Heteropolyoxometalate)

The two defective Keggin-structure $K_8[\gamma\text{-SiW}_{10}O_{36}] \cdot 12H_2O$ (1.5 g) was dissolved in 15 ml of deionized water at room temperature, and the pH was adjusted to 3.90 with an aqueous solution of nitric acid. Thereto was added a solution of 0.41 g of ferric nitrate nonahydrate in 2.5 ml of deionized water, and the mixture was stirred for 5 minutes. Then, 1.04 g of tetrabutylammonium nitrate (hereinafter, "TBA") was added in the form of a, and stirring was continued for 15 minutes. The resulting precipitate was filtered and dried at room temperature for 3 hours. The recovered solid was dissolved in 7.5 ml of acetonitrile, 150 ml of deionized water was gently added thereto, and the mixture was stirred on ice water for 30 minutes. The precipitate was recovered by filtration and dried at room temperature for 3 hours, and again the above-mentioned treatment with acetonitrile and deionized water was repeated to give a purified solid.
Au-POM $K_8[\gamma\text{-SiW}_{10}O_{36}] \cdot 12H_2O$ (1.5 g) was dissolved in 15 ml of deionized water and, then, 19.7 ml of an aqueous solution prepared by dissolving chloroauric acid in an aqueous solution of HCl to a concentration of 1,000 ppm was added thereto. The pH was then 0.66. Except for the above, Au-POM was prepared according to the procedure for producing Fe-POM.
Cr(III)-POM Cr(III)-POM was prepared according to the procedure for preparing Fe-POM except that the pH was adjusted to 3.80 and that an aqueous solution prepared by dissolving 0.4 g of chromium nitrate nonahydrate in 3.5 ml of deionized water was used instead of the aqueous solution of ferric nitrate nonahydrate.
Zn-POM Zn-POM was prepared according to the procedure for preparing Fe-POM except that the pH was adjusted to 3.2 with an aqueous solution of nitric acid and that an aqueous solution prepared by dissolving 0.3 g of zinc nitrate hexahydrate in 3.5 ml of deionized water was used instead of the aqueous solution of ferric nitrate nonahydrate.
La-POM (Defective Polyoxometallate-Coordinated La ion)

La-POM was prepared according to the procedure for preparing Fe-POM except that the pH was adjusted to 3.8 with an aqueous solution of nitric acid and that an aqueous solution prepared by dissolving 0.43 g of lanthanum nitrate hexahydrate in 3.5 ml of deionized water was used instead of the aqueous solution of ferric nitrate nonahydrate. Elemental analysis revealed that the coordination number was about 2 to 3.
Nd-POM (Defective Polyoxometallate-Coordinated Nd ion)

Nd-POM was prepared according to the procedure for preparing Fe-POM except that the pH was adjusted to 3.7 with an aqueous solution of nitric acid and that an aqueous solution prepared by dissolving 0.61 g of neodymium carbonate octahydrate in 10 ml of deionized water was used instead of the aqueous solution of ferric nitrate nonahydrate. Elemental analysis revealed that the coordination number was about 2 to 3.
Sm-POM (Defective Polyoxometallate-Coordinated Sm ion)

Sm-POM was prepared according to the procedure for preparing Fe-POM except that the pH was adjusted to 3.8 with an aqueous solution of nitric acid and that an aqueous solution prepared by dissolving 0.40 g of samarium acetate tetrahydrate in 5 ml of deionized water was used instead of the aqueous solution of ferric nitrate nonahydrate. Elemental analysis revealed that the coordination number was 2 to 3.

Pr-POM (Defective Polyoxometallate-Coordinated Pr ion)

Pr-POM was prepared according to the procedure for preparing Fe-POM except that the pH was adjusted to 3.5 with an aqueous solution of nitric acid and that an aqueous solution prepared by dissolving 0.42 g of praseodymium nitrate in 3.5 ml of deionized water was used instead of the aqueous solution of ferric nitrate nonahydrate. Elemental analysis revealed that the coordination number was about 2 to 3.

Yb-POM (Defective Polyoxometallate-Coordinated Yb ion)

Yb-POM was prepared according to the procedure for preparing Fe-POM except that the pH was adjusted to 3.6 with an aqueous solution of nitric acid and that an aqueous solution prepared by dissolving 0.38 g of ytterbium trichloride hexahydrate in 3.5 ml of deionized water was used instead of the aqueous solution of ferric nitrate nonahydrate. Elemental analysis revealed that the coordination number was about 2 to 3.

Eu-POM (Defective Polyoxometallate-Coordinated Eu ion)

Eu-POM was prepared according to the procedure for preparing Fe-POM except that the pH was adjusted to 3.4 with an aqueous solution of nitric acid and that an aqueous solution prepared by dissolving 0.43 g of europium trichloride hexahydrate in 5 ml of deionized water was used instead of the aqueous solution of ferric nitrate nonahydrate. Elemental analysis revealed that the coordination number was about 2 to 3.

Y-POM (Defective Polyoxometallate-Coordinated Y ion)

Y-POM was prepared according to the procedure for preparing Fe-POM except that the pH was adjusted to 3.7 with an aqueous solution of nitric acid and that an aqueous solution prepared by dissolving 0.30 g of yttrium trichloride hexahydrate in 3.5 ml of deionized water was used instead of the aqueous solution of ferric nitrate nonahydrate. Elemental analysis revealed that the coordination number was about 2 to 3.

Ce-POM (Defective Polyoxometallate-Coordinated Ce ion)

Ce-POM was prepared according to the procedure for preparing Fe-POM except that the pH was adjusted to 3.6 with an aqueous solution of nitric acid and that an aqueous solution prepared by dissolving 0.35 g of cerous acetate monohydrate in 15 ml of deionized water was used instead of the aqueous solution of ferric nitrate nonahydrate. Elemental analysis revealed that the coordination number was about 2 to 3.

Sn-POM (Preparation of Sn-Substituted Two Defective Type Heteropolyacid)

Sn-POM was prepared according to the procedure for preparing Fe-POM except that the pH was adjusted to 3.5 with an aqueous solution of nitric acid and that an aqueous solution prepared by dissolving 0.22 g of tin dichloride dihydrate in 10 ml of deionized water adjusted to pH 1.5 was used instead of the aqueous solution of ferric nitrate nonahydrate.

Mo-POM (Preparation of Mo-Substituted Two Defective Type Heteropolyacid)

Mo-POM was prepared according to the procedure for preparing Fe-POM except that the pH was adjusted to 3.8 with an aqueous solution of nitric acid and that a methanol solution prepared by dissolving 0.4 g of molybdenum acetonylacetone in 40 ml of methanol was used instead of the aqueous solution of ferric nitrate nonahydrate.

Ag-POM

Ag-POM was prepared according to the procedure for preparing Fe-POM except that the pH was adjusted to 3.4 with an aqueous solution of nitric acid and that an aqueous solution prepared by dissolving 0.17 g of silver nitrate in 5 ml of deionized water was used instead of the aqueous solution of ferric nitrate nonahydrate.

Sb-POM (Preparation of Sb-Substituted Two Defective Type Heteropolyacid)

Sb-POM was prepared according to the procedure for preparing Fe-POM except that the pH was adjusted to 3.4 with an aqueous solution of nitric acid and that an aqueous solution prepared by dissolving 0.3 g of antimony acetate in 5 ml of acetic acid was used instead of the aqueous solution of ferric nitrate nonahydrate.

Cu-POM (Preparation of Cu-Substituted Two Defective Type Heteropolyacid)

Cu-POM was prepared according to the procedure for preparing Fe-POM except that the pH was adjusted to 3.9 with an aqueous solution of nitric acid and that an aqueous solution prepared by dissolving 0.24 g of copper nitrate trihydrate in 5 ml of deionized water was used instead of the aqueous solution of ferric nitrate nonahydrate.

In-POM (Preparation of In-Substituted Two Defective Type Heteropolyacid)

In-POM was prepared according to the procedure for preparing Fe-POM except that the pH was adjusted to 3.9 with an aqueous solution of nitric acid and that an aqueous solution prepared by dissolving 0.3 g of indium acetate hydrate in 20 ml of deionized water was used instead of the aqueous solution of ferric nitrate nonahydrate.

Pd-POM

Pd-POM was prepared according to the procedure for preparing Fe-POM except that the pH was adjusted to 4.7 with an aqueous solution of nitric acid and that 50 ml of a solution prepared by dissolving palladium chloride in an aqueous solution of hydrochloric acid to a concentration of 1,000 ppm was used instead of the aqueous solution of ferric nitrate nonahydrate.

Mn(III)-POM (Preparation of Mn-Substituted Two Defective Type Heteropolyacid)

Mn(III)-POM was prepared according to the procedure for preparing Fe-POM except that the pH was adjusted to 3.8 with an aqueous solution of nitric acid and that an aqueous solution prepared by dissolving 0.5 g of potassium permanganate in 5 ml of deionized water was used instead of the aqueous solution of ferric nitrate nonahydrate.

Ru-POM (Preparation of Ru-Substituted Two Defective Type Heteropolyacid)

Ru-POM was prepared according to the procedure for preparing Fe-POM except that the pH was adjusted to 3.9 with an aqueous solution of nitric acid, that an acetonitrile solution prepared by dissolving 0.3 g of $[RuCl_2(p\text{-cymene})_2]$ in 5 ml of acetonitrile was used instead of the aqueous solution of ferric nitrate nonahydrate and that 2.05 g of TBA was used.

Re-POM

Re-POM was prepared according to the procedure for preparing Fe-POM except that an aqueous solution prepared by dissolving 0.27 g of $NaReO_4$ in 3 ml of deionized water was used instead of the aqueous solution of ferric nitrate nonahydrate.

$(TBA)_4[\gamma\text{-}SiW_{12}O_{40}]$

A defect-free catalyst was prepared by the method described in Inorganic Syntheses, vol. 27, p. 95.

$(TBA) [SiW_{11}O_{39}]$

One defective Keggin-structure $K_8[\beta_2\text{-}SiW_{11}O_{39}]\cdot14H_2O$ (4 g) prepared by the method described in Inorganic Syntheses, vol. 27, p. 91 was dissolved in 40 ml of deionized water at room temperature, 3 g of TBA was added thereto, and the mixture was stirred for 15 minutes, followed by filtration. The recovered solid was washed and purified according to the procedure for preparing the Fe-POM catalyst to give the desired catalyst.

(TBA) $[SiW_{10}O_{36}]$

The two defective Keggin-structure $K_8[\gamma\text{-}SiW_{10}O_{36}]\cdot12H_2O$ (4 g) was dissolved in 40 ml of deionized water at room temperature, and the pH was adjusted to 3.9 with an aqueous solution of nitric acid. Thereto was added 3.28 g of TBA, and the mixture was stirred for 15 minutes, followed by filtration. The recovered solid was washed and purified according to the procedure for preparing the Fe-POM catalyst to give the desired catalyst.

(TBA) $[\alpha\text{-}SiW_9O_{34}]$ $Na_8[\alpha\text{-}SiW_9O_{34}]_{23}\cdot H_2O$ (1.435 g, 0.5 mmol) was dissolved in 30 ml of deionized water and, then, 4.1 g of TBA was added. Then, the same procedure for preparing the Fe-POM comprising washing with acetonitrile and water, and purification was performed.

(TBA) $[SiW_{11}O_{39}Zn]$

One defective type $K_8[\beta_2\text{-}SiW_{11}O_{39}]\cdot14H_2O$ (1.63 g, 0.5 mmol) prepared by the method described in Inorganic Syntheses, vol. 27, p. 91 was dissolved in 30 ml of deionized water at room temperature, an aqueous solution prepared by dissolving 0.15 g of zinc nitrate hexahydrate in 5 ml of deionized water was added thereto and, after 5 minutes of stirring, 1.5 g of TBA was added, followed by 15 minutes of further stirring. Thereafter, the mixture was filtered and dried at room temperature to give a solid. This solid was washed and purified according to the procedure for preparing the Fe-POM catalyst to give the desired catalyst.

La-$[SiW_{11}O_{39}]$

One defective type $K_8[\beta_2\text{-}SiW_{11}O_{39}]\cdot14H_2O$ (1.63 g, 0.5 mmol) prepared by the method described in Inorganic Syntheses, vol. 27, p. 91 was dissolved in 30 ml of deionized water at room temperature, an aqueous solution prepared by dissolving 0.11 g of lanthanum nitrate hexahydrate in 5 ml of deionized water was added thereto and, after 5 minutes of stirring, 1.5 g of TBA was added, followed by 15 minutes of further stirring. Thereafter, the mixture was filtered and dried at room temperature to give a solid. This solid was washed and purified according to the procedure for preparing the Fe-POM catalyst to give the desired catalyst.

(TBA) $[SiMo_2VW_9O_{40}]$ (Preparation of Mo- and V-Substituted Heteropolyoxometalate)

$K_5[SiMo_2VW_9O_{40}]$ (0.15 g) prepared by the method described in Inorg. Chem., 31 (1992), p. 4128 was dissolved in 5 ml of deionized water at room temperature, 1.5 g of TBA was added thereto, and the mixture was stirred for 1 hour. Thereafter, the mixture was filtered under reduced pressure and dried at room temperature for 3 hours to give the desired compound as a catalyst.

(TBA) $[SiMoV_2W_9O_{40}]$ (Preparation of Mo- and V-Substituted Heteropolyoxometalate)

$NaVO_3$ (0.12 g) was dissolved in 10 ml of deionized water and the pH was adjusted to 2.0 by adding a 3 mol/l aqueous solution of HCl. Thereto was added gradually 3 g of $K_8[SiMo_2W_9O_{40}]$ prepared by the method described in Inorg. Chem., 31 (1992), p. 4128 for complete dissolution. A 1 mol/l AcOH-1 mol/l NaOAc buffer (2 ml) and a solution prepared by dissolving 0.12 g of $NaVO_3$ in 2 ml of deionized water were added to the above solution, and the mixture was stirred at 65° C. for 16 hours. After cooling to room temperature, 2 g of TBA was added and the mixture was stirred for 1 hour. The mixture was filtered under reduced pressure and dried at room temperature for 3 hours to give the desired compound as a catalyst.

Olefin Epoxidation Reaction

EXAMPLE 1

Propylene Epoxidation Reaction

The reaction temperature was 20° C. A 17.5-ml autoclave was charged with 8 μmoles of the V-POM catalyst, 6 ml of acetonitrile and 1,100 μmoles of 31% (by mass) hydrogen peroxide. The gaseous phase was filled with pure gaseous propylene under pressurization at $6\times10^5$ Pa, and the reaction was allowed to proceed while stirring the liquid phase. The amount of propylene charged on that occasion was 4,250 μmoles (obtainable by calculation based on the space volume of the autoclave and the pressure). During the reaction, the gaseous phase pressure was maintained at $6\times10^5$ Pa by adding gaseous propylene. After the start of the reaction, the autoclave inside was put back to ordinary pressure at regular intervals and, each time, the liquid phase was sampled and analyzed by gas chromatography. The product yield was calculated from the ratio between the number of moles of hydrogen peroxide charged at the start of reaction and the number of moles of the product. The selectivity for the product was calculated from the ratio between the total number of moles of all products and the number of moles of the each product. After 2 hours of reaction, the results were as follows: the propylene oxide (hereinafter, "PO") yield was 7.3% and the selectivity for PO was 98.5%. Other products were small amounts of acetaldehyde, propionaldehyde, acetone, isopropyl alcohol and propylene glycol. After 8 hours, the PO yield was 21.0% and the selectivity for PO was 98.7%. After further 24 hours, the PO yield was 24.6% and the selectivity for PO was 98.4%. The results after 8 hours are shown in Table 1. The performance of the catalyst was very good.

EXAMPLE 2

The reaction of Example 1 was carried out in the same manner except that hydrogen peroxide was charged in an increased amount of 4,000 μmoles. After 8 hours of reaction, the yield of PO was 24.1% and the selectivity for PO was 98.5%. It was thus revealed that the increase in proportion of hydrogen peroxide relative to propylene exerts little influence on the reaction results.

COMPARATIVE EXAMPLE 1

Propylene epoxidation reaction was carried out in the same manner as in Example 1 except that (TBA) $[SiW_{12}O_{40}]$ catalyst having no defective sites and containing no specific element (E), was used instead of the V-POM catalyst. The results after 8 hours were as shown in Table 1. It is evident that the activity is very low.

COMPARATIVE EXAMPLE 2

Propylene epoxidation reaction was carried out in the same manner as in Example 1 except that one defective type (TBA) $[SiW_{11}O_{39}]$ catalyst containing no specific element (E), was used instead of the V-POM catalyst. The results after 8 hours were shown in Table 1. Since the catalyst used is the one defective type and contains no specific element (E), its activity is very low.

COMPARATIVE EXAMPLE 3

Propylene epoxidation reaction was carried out in the same manner as in Example 1 except that three defective type (TBA) $[\alpha\text{-}SiW_9O_{34}]$ catalyst containing no specific element (E), was used instead of the V-POM catalyst. The results after 8 hours were shown in Table 1. Since the catalyst contains no specific element (E), the catalyst has no activity.

COMPARATIVE EXAMPLE 4

Propylene epoxidation reaction was carried out in the same manner as in Example 1 except that the Fe-POM catalyst was used instead of the V-POM catalyst. The results after 8 hours were shown in Table 1.

COMPARATIVE EXAMPLE 5

Propylene epoxidation reaction was carried out in the same manner as in Comparative Example 4 except that hydrogen peroxide was charged in an amount of 4,000 $\mu$moles. The results after 8 hours were shown in Table 1. It is evident that the selectivity for PO decreases with the increase in proportion of hydrogen peroxide relative to propylene.

COMPARATIVE EXAMPLE 6

Propylene epoxidation reaction was carried out in the same manner as in Example 1 except that the Mn(III)-POM catalyst was used instead of the V-POM catalyst. The results after 8 hours were shown in Table 1.

COMPARATIVE EXAMPLE 7

Propylene epoxidation reaction was carried out in the same manner as in Example 1 except that the Cu-POM catalyst was used instead of the V-POM catalyst. The results after 8 hours were shown in Table 1.

EXAMPLES 3 TO 15

Propylene epoxidation reaction was carried out in the same manner as in Example 1 except that the specific element (E)-containing Mo-, Pd-, Ni-, Co-, Cr-, Ag-, Au-, Zn-, In-, Sn-, Sb-, Ru- or Y-POM catalyst was used instead of the V-POM catalyst. The results after 8 hours of reaction are summarized in Table 1.

EXAMPLE 16

Propylene epoxidation reaction was carried out in the same manner as in Example 1 except that the La-POM catalyst containing La as the specific element (E) was used instead of the V-POM catalyst. The results after 8 hours of reaction are shown in Table 1.

EXAMPLE 17

Propylene epoxidation reaction was carried out in the same manner as in Example 16 except that hydrogen peroxide was charged in an amount of 4,000 $\mu$moles. The results after 8 hours were shown in Table 1. The increase in proportion of hydrogen peroxide relative to propylene exerted little influence on the yield.

EXAMPLES 18 TO 25

Propylene epoxidation reaction was carried out in the same manner as in Example 1 except that the specific element (E)-containing Ce-, Pr-, Nd-, Sm-, Eu- or Yb-POM catalyst or the V- and Mo-substituted three defective type catalyst (TBA) [SiMo$_2$VW$_9$O$_{40}$] or (TBA) [SiMoV$_2$W$_9$O$_{40}$] was used instead of the V-POM catalyst. The results after 8 hours of reaction are summarized in Table 1.

COMPARATIVE EXAMPLES 8 AND 9

Propylene epoxidation reaction was carried out in the same manner as in Example 1 except that the specific element-, Zn-substituted one defective (TBA) [SiW$_{11}$O$_{39}$Zn] catalyst (Comparative Example 8) or the La-substituted one defective La-[SiW$_{11}$O$_{39}$] catalyst (Comparative Example 9) was used instead of the V-POM catalyst. The results after 8 hours were as shown in Table 1. It is seen that even when substituted by the specific element Zn or La, the one defective type heteropolyoxometalates have no or a very low activity.

TABLE 1

| | | Propylene oxide yield after 8 hours (on H$_2$O$_2$ basis) | |
| --- | --- | --- | --- |
| | Catalyst | Molar yield of propylene oxide (%) | Molar selectivity for propylene oxide (%) |
| Ex. 1 | V—POM | 21.0 | 98.7 |
| Ex. 2 | V—PaM | 24.1 | 95.5 |
| Compar. Ex. 1 | (TBA) [SiW$_{12}$O$_{40}$] | 0.2 | 91.0 |
| Compar. Ex. 2 | (TBA) [SiW$_{11}$O$_{39}$] | 0.4 | 57.1 |
| Compar. Ex. 3 | (TBA) [SiW$_9$O$_{34}$] | 0.0 | 0.0 |
| Compar. Ex. 4 | Fe—POM | 11.5 | 64.3 |
| Compar. Ex. 5 | Fe—POM | 11.8 | 40.3 |
| Compar. Ex. 6 | Mn—POM | 6.1 | 50.6 |
| Compar. Ex. 7 | Cu—POM | 8.5 | 60.3 |
| Ex. 3 | Mo—POM | 79.5 | 95.5 |
| Ex. 4 | Pd—POM | 82.3 | 95.0 |
| Ex. 5 | Ni—POM | 50.6 | 86.0 |
| Ex. 6 | Co—POM | 55.1 | 61.0 |
| Ex. 7 | Cr(III)—POM | 48.0 | 66.0 |
| Ex. 8 | Ag—POM | 20.6 | 83.4 |
| Ex. 9 | Au—POM | 71.5 | 97.4 |
| Ex. 10 | Zn—POM | 81.2 | 98.6 |
| Ex. 11 | In—POM | 13.4 | 89.7 |
| Ex. 12 | Sn—POM | 27.8 | 88.6 |
| Ex. 13 | Sb—POM | 23.5 | 80.1 |
| Ex. 14 | Ru—POM | 79.0 | 97.8 |
| Ex. 15 | Y—POM | 82.4 | 89.6 |
| Ex. 16 | La—POM | 92.3 | 99.2 |
| Ex. 17 | La—POM | 93.0 | 98.9 |
| Ex. 18 | Ce—POM | 81.0 | 98.5 |
| Ex. 19 | Pr—POM | 75.9 | 97.8 |
| Ex. 20 | Nd—POM | 79.0 | 98.5 |
| Ex. 21 | Sm—POM | 82.8 | 98.1 |
| Ex. 22 | Eu—POM | 83.7 | 98.8 |
| Ex. 23 | Yb—POM | 89.9 | 99.5 |
| Ex. 24 | (TBA) [SiMo$_2$VW$_9$] | 18.7 | 89.0 |
| Ex. 25 | (TBA) [SiMoV$_2$W$_9$] | 19.1 | 88.3 |
| Compar. Ex. 8 | (TBA) [SiW$_{11}$Zn] | 0.0 | 0.0 |
| Compar. Ex. 8 | La—[SiW$_{11}$O$_{39}$] | 1.4 | 100.0 |

EXAMPLE 26

1-Butene Epoxidation Reaction

The reaction temperature was 20° C. A 17.5-ml autoclave was charged with 8 $\mu$moles of the La-POM catalyst, 6 ml of acetonitrile and 1,100 $\mu$moles of 31% (by mass) hydrogen peroxide. The gaseous phase was filled with pure gaseous propylene under pressurization at $3 \times 10^5$ Pa, and the reaction was allowed to proceed while stirring the liquid phase. During the reaction, the gaseous phase pressure was maintained at $3 \times 10^5$ Pa by adding gaseous 1-butene. After the start of the reaction, the autoclave inside was put back to ordinary pressure at regular intervals and, each time, the liquid phase was sampled and analyzed by gas chromatography. The product yield was calculated from the ratio between the number of moles of hydrogen peroxide charged at the start of reaction and the number of moles of the product. The selectivity for the product was calculated from the ratio between the total number of moles of all products and the number of moles of the each product. After 2 hours of reaction, the results were as follows: the 1-butene oxide (hereinafter, "BO") yield was 6.4% and the selectivity for BO was 100.0%. After 8 hours, the BO yield was 76.3% and the selectivity for BO was 100.0%.

EXAMPLE 27
1-Hexene Epoxidation Reaction

The La-POM catalyst (8 µmoles), 6 ml of acetonitrile and 200 µmoles of 31% (by mass) hydrogen peroxide were charged into a Pyrex test tube. Thereto was added 1,000 µmoles of 1-hexene and, after substitution of the gaseous phase with argon gas, the tube was immersed in a water bath at 32° C. and the reaction was allowed to proceed while thoroughly stirring the liquid phase. After the start of the reaction, the liquid phase was assayed for products at regular intervals by gas chromatography. The product yield was calculated from the ratio between the number of moles of hydrogen peroxide charged at the start of reaction and the number of moles of the each product. The selectivity for the product was calculated from the ratio between the total number of moles of all products and the number of moles of the each product. After 2 hours of reaction, the results were as follows: the 1,2-epoxyhexane (hereinafter, "HO") yield was 4.4% and the selectivity for HO was 100.0%. After 8 hours, the HO yield was 34.7% and the selectivity for HO was 100.0%. After 24 hours, the HO yield was 72.7% and the selectivity for HO was 100%.

EXAMPLE 28
1-Hexene Epoxidation Reaction

1-Hexene epoxidation reaction was carried out in the same manner as in Example 27 except that the Re-POM catalyst was used instead of the La-POM catalyst. After 7 hours of reaction, the results were as follows: the HO yield was 1.0% and the selectivity for HO was 100%.

EXAMPLES 29 TO 31
Cis-2-Octene Epoxidation Reaction

Cis-2-Octene epoxidation reaction was carried out in the same manner as in Example 27 except that cis-2-octene was used instead of 1-hexene and that the Au-POM catalyst (Example 29), Sn-POM catalyst (Example 30) or Zn-POM catalyst (Example 31) was used instead of the La-POM catalyst. After 6 hours of reaction, the results were as follows: for the Au-POM catalyst, the 2-epoxyoctane yield was 84.5%, the selectivity for 2-epoxyoctane was 96.0% and the cis-form content was higher than 99.0%; for the Sn-POM catalyst, the 2-epoxyoctance yield was 5.9%, the selectivity for 2-epoxyoctane was 82.0% and the cis-form content was 97.0%; and for the Zn-POM catalyst, the 2-epoxyoctane yield was 83.5%, the selectivity for 2-epoxyoctane was 97.0% and the cis-form content was higher than 99%.

EXAMPLE 32
Allyl Alcohol Epoxidation Reaction

The V-POM catalyst (8 µmoles), 6 ml of acetonitrile and 200 µmoles of 31% (by mass) hydrogen peroxide were charged into a Pyrex test tube. Thereto was added 1,000 µmoles of allyl alcohol and, after substitution of the gaseous phase with argon gas, the tube was immersed in a water bath at 32° C. and the reaction was allowed to proceed while thoroughly stirring the liquid phase. After the start of the reaction, the liquid phase was assayed for products at regular intervals by gas chromatography. The product yield was calculated from the ratio between the number of moles of hydrogen peroxide charged at the start of reaction and the number of moles of the product. After 24 hours of reaction, the results were as follows: the glycidol yield was 1.2% and the acrolein yield was 0.8%.

EXAMPLES 33 AND 34

Allyl alcohol epoxidation reaction was carried out in the same manner as in Example 32 except that La-POM (Example 33) or Yb-POM (Example 34) was used as the catalyst. After 24 hours of reaction, the results were as follows: for the La-POM catalyst (Example 33), the glycidol yield was 1.7% and the acrolein yield was 9.1%; for the Yb—POM catalyst (Example 34), the glycidol yield was 6.4% and the acrolein yield was 11.7%.

COMPARATIVE EXAMPLE 10

Allyl alcohol epoxidation reaction was carried out in the same manner as in Example 32 except that the specific element La-containing one defective catalyst La-$[SiW_{11}O39]$ was used instead of the V-POM catalyst. After 24 hours of reaction, the results were poor; the glycidol yield was as low as 0.3% and the acrolein yield was as low as 0.2%.

EXAMPLE 35
Styrene Epoxidation Reaction

Styrene epoxidation reaction was carried out in the same manner as in Example 27 except that styrene was used instead of 1-hexene and that V-POM was used as the catalyst. After 24 hours of reaction, the results were as follows: the styrene oxide yield was 1.8%, the acetophenone yield was 0.4% and the benzaldehyde yield was 2.1%.

EXAMPLE 36
Cyclohexene Epoxidation Reaction

Cyclohexene epoxidation was carried out in the same manner as in Example 27 except that cyclohexene was used instead of 1-hexene, that as the catalyst, $SiO_2$/V-POM was used instead of La-POM and that as the solvent, benzene was used instead of acetonitrile. After 4 hours of reaction, the results were as follows: the cyclohexene oxide yield was 1.5% and the selectivity for cyclohexene oxide was 22.3%. After the reaction, the catalyst was separated by filtration. The content of vanadium and tungsten in the filtrate was not more than 0.1% (relative to the amount of catalyst used).

(I) Catalyst Preparation $Na_9[A-PW_9O_{34}]$ (Three Defective Keggin-Structure Heteropolyoxometalate)

The title compound was prepared by the synthetic method described in Inorganic Syntheses, vol. 27 (1990), p. 100. $NaWO_4 \cdot 2H_2O$ (120 g) was dissolved in 150 g of deionized water, 4 ml of phosphoric acid was then added gradually, and the pH was adjusted to 7.5 by addition of 22.5 ml of acetic acid, followed by 1 hour of stirring. The desired product was filtered off under reduced pressure and dried at room temperature for 4 hours (yield 79.5 g).

$Cs_7[\gamma-PW_{10}O_{36}]$ (Two Defective Keggin-Structure Heteropolyoxometalate)

The title compound was prepared by the synthetic method described in Inorganic Syntheses, vol. 27 (1990), p. 101. $Cs_6[P_2W_5O_{23}]$ (18.8 g) was dissolved in 37.5 g of deionized water. The solution was stirred under reflux for 24 hours, and the solid was filtered off and dried at room temperature to give 4.0 g of the desired product.

Sodium acetate (4.1 g) was dissolved in 50 g of deionized water, and acetic acid was added until the pH became 4.8. Thereto were added 1.5 g of $NaVO_3$ and 10 g of $Na_9[A-PW_9O_{34}]$, and the mixture was stirred for 48 hours. Separately, 7.74 g of tetrabutylammonium bromide (hereinafter, "TBA") was dissolved in 50 g of deionized water, and the aqueous solution was added to the above solution. The mixture was stirred for 30 minutes, and the mixture was filtered under reduced pressure and dried overnight at room temperature to give the desired catalyst.

(TBA)$_5$K$_2$[PTi$_2$W$_{10}$O$_{40}$]·6H$_2$O (Ti-Substituted Heteropolyoxometalate)

The title compound was prepared by the production method described in J. Mol. Catal. A: Chemical, 114 (1996), p. 237. Thus, 10 g of K$_7$[PTi$_2$W$_{10}$O$_{40}$]·6H$_2$O (prepared by the preparation method described in Inorg. Chem., 22 (1983), p. 818) was dissolved in 160 ml of deionized water. To the aqueous solution was added 10 g of tetrabutylammonium bromide, the pH was adjusted to 5.0 with a 2 mol/l aqueous solution of HCl, and the white precipitate was filtered off. The solid was washed with 20 ml of deionized water twice, dried in the air and then recrystallized from ethanol-acetone (1/1, volume/volume) to give the desired catalyst.

Cs$_5$[γ-PV$_2$W$_{10}$O$_{40}$] (V-Substituted Heteropolyoxometalate)

NaVO$_3$ (0.16 g) was dissolved in 10 g of deionized water at 70° C., the solution was cooled to room temperature, and a 3 mol/l aqueous solution of HCl was added drop by drop thereto to adjust the pH to 0.8. To this solution was added gradually 2 g of Cs$_7$[PW$_{10}$O$_{36}$] separately synthesized over 20 minutes, and the mixture was further stirred intensely for 30 minutes. Then, the mixture was filtered under reduced pressure and dried for 3 to 4 hours to give 0.103 g of the desired compound.

(TBA)$_5$[γ-PV$_2$W$_{10}$O$_{40}$] (V-Substituted Heteropolyoxometalate)

NaVO$_3$ (20 mg) was dissolved in 10 g of deionized water at 70° C., the solution was cooled to room temperature, and a 3 mol/l aqueous solution of HCl was added drop by drop thereto to adjust the pH to 2. To this solution was added 0.25 g of Cs$_5$[γ-PV$_2$W$_{10}$O$_{40}$], and the mixture was stirred for 10 minutes. Then, the insoluble materials were filtered off, 0.24 f of TBA was added to the filtrate, and the mixture was stirred vigorously for 1 hour. The mixture was filtered under reduced pressure and dried overnight to give 0.12 g of the desired compound.

TBA Salt of Re-Containing [α-PW$_9$O$_{34}$] (Hereinafter Referred to as TBA-Re-[α-PW$_9$O$_{34}$])

Sodium acetate (0.41 g) was dissolved in 5 g of deionized water, and the solution was adjusted to pH 4.8 by adding about 0.3 ml of acetic acid. To this solution were added 0.34 g of NaReO$_4$ and 1.0 g of Na$_9$[A-PW$_9$O$_{34}$] and, after 24 hours of stirring, 1.5 g of TBA was added and the mixture was further stirred for 1 hour. Thereafter, the mixture was filtered under reduced pressure, and the recovered solid was dried at room temperature for 4 hours to give 1.5 g of the desired product as a catalyst.

TBA Salt of In-Containing [α-PW$_9$O$_{34}$] (Hereinafter Referred to as TBA-In-[α-PW$_9$O$_{34}$])

Sodium acetate (0.41 g) was dissolved in 5 g of deionized water, and the solution was adjusted to pH 4.8 by adding about 0.3 ml of acetic acid. To this solution was added a solution of 0.44 g of indium acetate and 1.0 g of Na$_9$[A-PW$_9$O$_{34}$] in deionized water acidified with nitric acid and, after 24 hours of stirring, 1.5 g of TBA was added and the mixture was further stirred for 1 hour. Thereafter, the mixture was filtered under reduced pressure, and the recovered solid was dried at room temperature for 4 hours to give the desired product as a catalyst.

TBA Salt of Bi-Containing [α-PW$_9$O$_{34}$] (Hereinafter Referred to as TBA-Bi-[α-PW$_9$O$_{34}$])

Sodium acetate (0.41 g) was dissolved in 5 g of deionized water, and the solution was adjusted to pH 4.8 by adding about 0.3 ml of acetic acid. To this solution was added a solution of 0.73 g of bismuth nitrate pentahydrate and 1.0 g of Na$_9$[A-PW$_9$O$_{34}$] in deionized water acidified with nitric acid and, after 24 hours of stirring, 1.5 g of TBA was added and the mixture was further stirred for 1 hour. Thereafter, the mixture was filtered under reduced pressure, and the recovered solid was dried at room temperature for 4 hours to give the desired product as a catalyst.

Cs$_5$[β-P{Fe(OH$_2$)}$_2$W$_{10}$O$_{38}$]

Ferric nitrate nonahydrate (0.14 g) was dissolved in 5 g of deionized water and the solution was adjusted to pH 0.8 by adding 2 or 3 drops of concentrated nitric acid. To this solution was added gradually 0.5 g of Cs$_7$[γ-PW$_{10}$O$_{36}$] synthesized separately over 15 minutes, and the mixture was further stirred intensely for 1 hour. The mixture was filtered under reduced pressure and dried for 3 to 4 hours to give 0.13 g of the desired compound.

Cs salt of La-containing [γ-PW$_{10}$O$_{36}$] (Hereinafter Referred to as Cs—La-[γ-PW$_{10}$O$_{36}$])

Lanthanum nitrate hexahydrate (10 g) was dissolved in 10 g of deionized water, and the solution was adjusted to pH 2.0 with a 6 mol/l aqueous solution of HCl. Thereto was added gradually 0.5 g of Cs$_7$[γ-PW$_{10}$O$_{36}$] over 15 minutes and, the mixture was further stirred intensely for 1 hour. Thereafter, the mixture was filtered under reduced pressure, and the recovered solid was dried at room temperature for 4 hours to give 0.08 g of the desired product as a catalyst.

Cs Salt of Re-Containing [γ-PW$_{10}$O$_{36}$] (Hereinafter Referred to as Cs—Re-[γ-PW$_{10}$O$_{36}$])

NaReO$_4$ (0.1 g) was dissolved in 10 g of deionized water, and the solution was adjusted to pH 2.0 by adding a 6 mol/l aqueous solution of HCl. Thereto was added gradually 0.5 g of Cs$_7$[γ-PW$_{10}$O$_{36}$] over 15 minutes and the mixture was further stirred for 1 hour. Thereafter, the mixture was filtered under reduced pressure, and the recovered solid was dried at room temperature for 4 hours to give 0.16 g of the desired product as a catalyst.

Cs Salt of La-Containing [A-PW$_9$O$_{34}$] (Hereinafter Referred to as Cs—La-[A-PW$_9$O$_{34}$])

Sodium acetate (0.41 g) was dissolved in 5 g of deionized water, and the solution was adjusted to pH 4.8 by adding 0.3 ml of acetic acid. To this solution were added 0.5 g of lanthanum nitrate hexahydrate and 1.0 g of Na$_9$[A-PW$_9$O$_{34}$] and, after 24 hours of stirring, 1.5 g of TBA was added, and the mixture was further stirred for 1 hour. Thereafter, the mixture was filtered under reduced pressure, and the recovered solid was dried at room temperature for 4 hours to give 1.09 g of the desired product as a catalyst.

Cs$_5$[β-PV$_2$W$_{10}$O$_{40}$] (V-Substituted Keggin Structure)

Cs$_5$[γ-PV$_2$W$_{10}$O$_{40}$] (0.15 g) was dissolved in 5 ml of deionized water and, after 60 hours of stirring at room temperature, the solution was concentrated to about 1 ml, and the concentrate was cooled at 0° C. for 1 hour. The solid precipitate was filtered under reduced pressure and dried at room temperature to give 0.08 g of the desired product as a catalyst.

Cs$_6$[α-1,2,3-PV$_3$W$_9$O$_{40}$] (V-Substituted Keggin Structure)

The title compound was prepared by the synthetic method described in Inorganic Syntheses, vol. 27 (1990), p. 100. Thus, 4.1 g of NaOAc was dissolved in 50 g of deionized water, and the solution was adjusted to pH 4.8 by further addition of 3 ml of acetic acid. Thereto were added 1.52 g of NaVO$_3$ and 10.0 g of Na$_9$[A-PW$_9$O$_{34}$], and the mixture was stirred for 48 hours. The impurities were removed by filtration, a solution of 4 g of CsCl in 5 g of deionized water was added to the filtrate, and the mixture was stirred for 30 minutes. The mixture was filtered under reduced pressure and dried at room temperature for 4 hours to give 9.8 g of the desired product as a catalyst.
Cs Salt of Zn-Containing [γ-PW$_{10}$O$_{36}$], Cs Salt of Mo-Containing [γ-PW$_{10}$O$_{36}$], Cs Salt of Rh-Containing [γ-PW$_{10}$O$_{36}$] and Cs Salt of Ir-Containing [γ-PW$_{10}$O$_{36}$] (Hereinafter Referred to as Cs-Zn-[γ-PW$_{10}$O$_{36}$], Cs-Mo-[γ-PW$_{10}$O$_{36}$], Cs-Rh-[γ-PW$_{10}$O$_{36}$] and Cs-Ir-[γ-PW$_{10}$O$_{36}$], Respectively)

The title compounds were prepared by the production method of the Cs salt of La-containing [PW$_{10}$O$_{36}$]. Zinc nitrate hexahydrate (0.11 g), molybdenum oxide acetylacetonate (0.12 g), rhodium trichloride trihydrate (0.077 g) or iridium tetrachloride (0.12 g) was used respectively instead of lanthanum nitrate hexahydrate.

Olefin Epoxidation Reaction

EXAMPLE 37
Propylene Epoxidation Reaction

The reaction temperature was 20° C. A 17.5-ml autoclave was charged with 8 μmoles of the (TBA)$_5$[α-PV$_2$W$_{10}$O$_{40}$] catalyst, 6 ml of acetonitrile and 1,100 μmoles of 31% (by mass) hydrogen peroxide. Pure gaseous propylene was charged into the gaseous phase portion under pressurization at 6×10$^5$ Pa, and the reaction was allowed to proceed while stirring the liquid phase. The amount of propylene charged on that occasion was 4,250 μmoles (obtainable by calculation based on the space volume of the autoclave and the pressure). During the reaction, the gaseous phase pressure was maintained at 6×10$^5$ Pa by supplementing with gaseous propylene. After the start of the reaction, the autoclave inside was put back to ordinary pressure at regular intervals and, each time, the liquid phase was analyzed by gas chromatography. The product yield was calculated from the ratio between the number of moles of hydrogen peroxide charged at the start of reaction and the number of moles of the product. The selectivity for the product was calculated from the ratio between the total number of moles of all products and the number of moles of the each product. After 2 hours of reaction, the results were as follows: the propylene oxide (hereinafter, "PO") yield was 1.4% and the selectivity for PO was 98.6%. Other products were small amounts of acetaldehyde, propionaldehyde, acetone, isopropyl alcohol and propylene glycol. After 8 hours, the PO yield was 16.7% and the selectivity for PO was 98.5%. Further, after 24 hours, the PO yield was 20.1% and the selectivity for PO was 98.4%. These results are shown in Table 2.

EXAMPLE 38

Propylene epoxidation reaction was carried out in the same manner as in Example 37 except that (TBA)$_6$[α-PV$_3$W$_9$O$_{40}$] was used instead of the (TBA)$_5$[α-PV$_2$W$_{10}$O$_{40}$] catalyst. The results after 2 hours, 8 hours and 24 hours of reaction are shown in Table 2.

EXAMPLE 39
1-Hexene Epoxidation Reaction

The (TBA)-Re-[α-PW$_9$O$_{34}$] catalyst (8 μmoles), 6 ml of acetonitrile and 200 μmoles of 31% (by mass) hydrogen peroxide were charged into a Pyrex test tube. Thereto was added 1,000 μmoles of 1-hexene and, after substitution of the gaseous phase with argon gas, the tube was immersed in a water bath at 32° C. and the reaction was allowed to proceed while thoroughly stirring the liquid phase. After the start of the reaction, the liquid phase was assayed for products at regular intervals by gas chromatography. After 24 hours of reaction, the results were as follows: the 1,2-epoxyhexane (hereinafter, "HO") yield was 7.25% and the selectivity for HO was 100.0%. After 48 hours, the HO yield was 17.0% and the selectivity for HO was 100.0%. These results are shown in Table 3.

EXAMPLES 40 TO 43

1-Hexene epoxidation reaction was carried out in the same manner as in Example 39 except that the Cs$_5$[γ-PV$_2$W$_{10}$O$_{40}$], Cs—Re-[γ-PW$_{10}$O$_{36}$], Cs—La-[γ-PW$_{10}$O$_{36}$] or TBA-La-[α-PW$_9$O$_{34}$] catalyst was used instead of the (TBA)-Re-[α-PW$_9$O$_{34}$] catalyst. The results are shown in Table 3.

COMPARATIVE EXAMPLE 11

1-Hexene epoxidation reaction was carried out in the same manner as in Example 39 except that the CS$_7$[γ-PW$_{10}$O$_{36}$] catalyst was used instead of the (TBA)-Re-[α-PW$_9$O$_{34}$] catalyst. The results are shown in Table 3.

COMPARATIVE EXAMPLE 12

1-Hexene epoxidation reaction was carried out in the same manner as in Example 39 except that the Na$_9$[A-PW$_9$O$_{34}$] catalyst was used instead of the (TBA)-Re-[α-PW$_9$O$_{34}$] catalyst. The results are shown in Table 3.

COMPARATIVE EXAMPLE 13

1-Hexene epoxidation reaction was carried out in the same manner as in Example 39 except that the (TBA)$_5$K$_2$[PTi$_2$W$_{10}$O$_{40}$].6H$_2$O catalyst was used instead of the (TBA)-Re-[α-PW$_9$O$_{34}$] catalyst. The results are shown in Table 3. As is evident from the results of Comparative Examples 11, 12 and 13, the catalysts containing no specific element E have very low reaction activity.

EXAMPLE 44

Cyclohexene epoxidation was carried out in the same manner as in Example 39 except that cyclohexene was used instead of 1-hexene. After 8 hours, the cyclohexane oxide yield was 44.8%, the selectivity for cyclohexane oxide was 100%. After 24 hours, the cyclohexane oxide yield was 88.5% and the selectivity for cyclohexane oxide was 99.6%. After 48 hours, the cyclohexane oxide yield was 99.5% and the selectivity for cyclohexane oxide was 99.6%. These results are shown in Table 4.

EXAMPLES 45 TO 54

Cyclohexene epoxidation reaction was carried out in the same manner as in Example 44 except that the Cs$_5$[γ-PV$_2$W$_{10}$O$_{40}$], (TBA)$_5$[β-PV$_2$W$_{10}$O$_{40}$], Cs-Zn-[γ-PW$_{10}$O$_{36}$], Cs-Mo-[γ-PW$_{10}$O$_{36}$], Cs—La-[γ-PW$_{10}$O$_{36}$], Cs-Rh-[γ-PW$_{10}$O$_{36}$], Cs-Ir-[γ-PW$_{10}$O$_{36}$], Cs—Re-[γ-PW$_{10}$O$_{36}$], (TBA)-In-[α-PW$_9$O$_{34}$] or (TBA)-Bi-[α-PW$_9$O$_{34}$] catalyst was used instead of the catalyst used in Example 44. The results are shown in Table 4.

EXAMPLE 55
Allyl Alcohol Epoxidation Reaction

The Cs$_5$[γ-PV$_2$W$_{10}$O$_{40}$] catalyst (8 μmoles), 6 ml of acetonitrile and 200 μmoles of 31% (by mass) hydrogen peroxide were charged into a Pyrex test tube. Thereto was added 1,000 μmoles of allyl alcohol and, after substitution of the gaseous phase with argon gas, the tube was immersed in a water bath at 32° C. and the reaction was allowed to proceed while thoroughly stirring the liquid phase. After the start of the reaction, the liquid phase was assayed for products at regular intervals by gas chromatography. The product yield was calculated from the ratio between the number of moles of hydrogen peroxide charged at the start of reaction and the number of moles of the product. After 7 hours of reaction, the results were as follows: the glycidol yield was 5.6% and the acrolein yield was 26.1%. After 24 hours, the glycidol yield was 5.6% and the acrolein yield was 27.4%. These results are shown in Table 5.

EXAMPLES 56 AND 57

Allyl alcohol epoxidation reaction was carried out in the same manner as in Example 55 except that $Cs_5[\mu\text{-}P\{Fe(OH_2)\}_2W_{10}O_{38}]$ or $(TBA)_6[\alpha\text{-}PV_3W_9O_{40}]$ was used instead of the $Cs_5[PV_2W_{10}O_{40}]$ catalyst. The results are shown in Table 5.

EXAMPLE 58
Styrene Epoxidation Reaction

Styrene epoxidation was carried out in the same manner as in Example 55 except that styrene was used instead of allyl alcohol. After 7 hours of reaction, the results were as follows: the styrene oxide yield was 1.85%, the acetophenone yield was 0.6%, and the benzaldehyde yield was 2.2%. After 24 hours, the styrene oxide yield was 5.75%, the acetophenone yield was 0.5%, and the benzaldehyde yield was 7.25%. These results are shown in Table 6.

EXAMPLES 59 AND 60

Styrene epoxidation reaction was carried out in the same manner as in Example 58 except that $Cs_5[\beta\text{-}P\{Fe(OH_2)\}_2W_{10}O_{38}]$ or $(TBA)_6[\alpha\text{-}PV_3W_9O_{40}]$ was used as the catalyst. The results are shown in Table 6.

TABLE 2

| | Catalyst | Reaction time (hrs) | Molar yield of PO (%) | Molar selectivity for PO (%) |
|---|---|---|---|---|
| Ex. 37 | $(TBA)_5[\alpha\text{-}PV_2W_{10}O_{40}]$ | 2 | 1.4 | 98.6 |
| | | 8 | 16.7 | 98.5 |
| | | 24 | 20.1 | 98.4 |
| Ex. 38 | $(TBA)_6[\alpha\text{-}PV_3W_9O_{40}]$ | 2 | 2.7 | 98.4 |
| | | 8 | 18.9 | 98.7 |
| | | 24 | 22.8 | 98 |

In Table 2, PO represents propylene oxide.

TABLE 3

| | Catalyst | Reaction time (hrs) | Molar yield of HO (%) | Molar selectivity for HO (%) |
|---|---|---|---|---|
| Ex. 39 | $(TBA)\text{-}Re\text{-}[\alpha\text{-}PW_9O_{34}]$ | 24 | 7.25 | 100 |
| | | 48 | 17 | 100 |
| Ex. 40 | $Cs_5[\gamma\text{-}PV_2W_{10}O_{40}]$ | 8 | 1.1 | 100 |
| | | 24 | 4.1 | 100 |
| Ex. 41 | $Cs\text{—}Re\text{-}[\gamma\text{-}PW_{10}O_{36}]$ | 7 | 3.5 | 100 |
| | | 24 | 13.5 | 100 |
| Ex. 42 | $Cs\text{—}La\text{-}[\gamma\text{-}PW_{10}O_{36}]$ | 24 | 1.35 | 100 |
| | | 48 | 2.2 | 100 |
| Ex. 43 | $(TBA)\text{-}La\text{-}[\gamma\text{-}PW_{10}O_{36}]$ | 24 | 0.4 | 100 |
| | | 48 | 0.7 | 100 |
| Compar. Ex. 11 | $Cs_7[\gamma\text{-}PW_{10}O_{36}]$ | 24 | 0 | — |
| | | 48 | 0.05 | 100 |
| Compar. Ex. 12 | $Na_9[A\text{—}PW_9O_{34}]$ | 24 | 0 | — |
| | | 48 | 0 | — |
| Compar. Ex. 13 | $(TBA)_5K_2[PTi_2W_{10}O_{40}]6H_2O$ | 24 | 0 | — |
| | | 48 | 0 | — |

In Table 3, HO represents 1,2-epoxyhexane.

TABLE 4

| | Catalyst | Reaction time (hrs) | Molar yield of c—HO (%) | Molar selectivity for c—HO (%) |
|---|---|---|---|---|
| Ex. 44 | $(TBA)\text{-}Re\text{-}[\alpha\text{-}PW_9O_{34}]$ | 8 | 44.8 | 100 |
| | | 24 | 88.5 | 99.6 |
| | | 48 | 99.5 | 99.6 |
| Ex. 45 | $Cs_5[\gamma\text{-}PV_2W_{10}O_{40}]$ | 8 | 9.4 | 95.9 |
| | | 24 | 29.5 | 6.8 |
| Ex. 46 | $(TBA)_5[\beta\text{-}PV_2W_{10}O_{40}]$ | 8 | 3.3 | 64.7 |
| | | 24 | 3.4 | 58.1 |
| Ex. 47 | $Cs\text{—}Zn\text{-}[\gamma\text{-}PW_{10}O_{36}]$ | 8 | 27.9 | 100 |
| | | 24 | 54 | 100 |
| Ex. 48 | $Cs\text{—}Mo\text{-}[\gamma\text{-}PW_{10}O_{35}]$ | 8 | 27.2 | 100 |
| | | 24 | 47.6 | 99.3 |
| Ex. 49 | $Cs\text{—}La\text{-}[\gamma\text{-}PW_{10}O_{36}]$ | 8 | 1.1 | 100 |
| | | 24 | 2.35 | 100 |
| Ex. 50 | $Cs\text{—}Rh\text{-}[\gamma\text{-}PW_{10}O_{36}]$ | 8 | 14.9 | 95.2 |
| | | 24 | 20.2 | 97.3 |
| Ex. 51 | $Cs\text{—}Ir\text{-}[\gamma\text{-}PW_{10}O_{36}]$ | 8 | 2.5 | 84.7 |
| | | 24 | 7.75 | 3.9 |

TABLE 4-continued

| Catalyst | | Reaction time (hrs) | Molar yield of c—HO (%) | Molar selectivity for c—HO (%) |
|---|---|---|---|---|
| Ex. 52 | Cs—Re-[γ-PW$_{10}$O$_{36}$] | 8 | 6.75 | 100 |
| | | 24 | 14.3 | 100 |
| Ex. 53 | (TBA)-In-(α-PW$_9$O$_{34}$] | 8 | 1.53 | 99.4 |
| | | 24 | 4.3 | 95.6 |
| Ex. 54 | (TSA)-Bi-[α-PW$_9$O$_{34}$] | 8 | 1.02 | 98.1 |
| | | 24 | 3.5 | 87.5 |

In table 4, c-HO represents cyclohexane oxide.

TABLE 5

| Catalyst | | Reaction time (hrs) | Molar yield of glycidol (%) | Molar yield of acrolein (%) |
|---|---|---|---|---|
| Ex. 55 | Cs$_5$[γ-PV$_2$W$_{10}$O$_{40}$] | 7 | 5.6 | 26.1 |
| | | 24 | 5.6 | 27.4 |
| Ex. 56 | Cs$_5$[β-P[Fe(OH$_2$)$_2$]W$_{10}$O$_{38}$] | 7 | 2.65 | 7.45 |
| | | 24 | 2.3 | 6.6 |
| Ex. 57 | (TBA)$_8$[α-PV$_3$W$_9$O$_{40}$] | 7 | 0 | 4.15 |
| | | 24 | 1.5 | 4.7 |

TABLE 6

| Catalyst | | Reaction time (hrs) | Molar yield of SO (%) | Molar yield of ACP (%) | Molar yield of BA (%) |
|---|---|---|---|---|---|
| Ex. 55 | Cs$_5$[γ-PV$_2$W$_{10}$O$_{40}$] | 7 | 1.85 | 0.6 | 2.2 |
| | | 24 | 5.75 | 0.5 | 7.25 |
| Ex. 56 | Cs$_5$[β-P{Fe(OH$_2$)$_2$}W$_{10}$O$_{38}$] | 7 | 0.95 | 0 | 0.33 |
| | | 24 | 1.55 | 0 | 0.63 |
| Ex. 57 | (TBA)$_6$[α-PV$_3$W$_9$O$_{40}$] | 7 | 0.4 | 0 | 4.1 |
| | | 24 | 1.4 | 0 | 5.65 |

In Table 6, SO stands for styrene oxide, ACP for acetophenone, and BA for benzaldehyde.

EFFECT OF THE INVENTION

In producing an epoxy compound by oxidizing a compound having at least one ethylenic double bond with an oxidizing agent, the catalyst of the invention, which has the above constitution, is capable of producing an epoxy compound in high yield and improving the utilization efficiency of the oxidizing agent. The method of the invention for producing an epoxy compound, which has the above constitution, is useful as a production method for providing epoxy compounds which are used as intermediates or raw materials for the production of various industrial products.

What is claimed is:

1. A catalyst for producing an epoxy compound by oxidizing a compound having at least one ethylenic double bond with an oxidizing agent, which comprises a polyatom-containing heteropolyoxometalate anion (A1) having two defective and/or three defective structure sites and containing silicon as the heteroatom, and an element (E1) is at least one element selected from the group consisting of vanadium, tantalum, niobium, antimony, bismuth, chromium, molybdenum, selenium, tellurium, rhenium, cobalt, nickel, ruthenium, rhodium, palladium, osmium, platinum, iridium, silver, gold, zinc, aluminum, gallium, indium, scandium, yttrium, titanium, zirconium, hafnium, germanium, tin and lanthanoids, and being different from the polyatom.

2. A method of producing an epoxy compound by oxidizing a compound having at least one ethylenic double bond with an oxidizing agent, wherein said method of producing the epoxy compound comprises using the catalyst according to claim 1.

3. The catalyst for producing an epoxy compound according to claim 1, wherein said polyatom-containing heteropolyoxometalate anion having two defective and/or three defective structure sites and containing silicon as the heteroatom being a Keggin-structure heteropolyoxometalate anion represented by the following general formula (1):

$$[SiM_{10}O_{36}]^{q-} \quad (1)$$

and/or the following general formula (2):

$$[SiM_9O_{34}]^{q-} \quad (2)$$

in the formulas (1) and (2), Si represents a silicon atom, Ms are the same or different and each represents at least one element selected from the group consisting of molybdenum, tungsten, vanadium and niobium and q is a positive integer.

4. A method of producing an epoxy compound by oxidizing a compound having at least one ethylenic double bond with an oxidizing agent, wherein said method of producing the epoxy compound comprises using the catalyst according to claim 3.

5. A catalyst for producing an epoxy compound by oxidizing a compound having at least one ethylenic double bond with an oxidizing agent, which comprises a heteropolyoxometalate anion (A2) containing phosphorus as a heteroatom and molybdenum and/or tungsten as a polyatom and having two defective and/or three defective structure sites, and an element (E2) being at least one element selected from the group consisting of elements of the fourth to sixth periods of group IIIa, elements of the fourth to sixth periods of groups VIa to VIII, elements of the fourth to sixth periods of groups Ib to IIb, elements of the third to sixth periods of group IIIb, and elements of the fourth to sixth periods of groups IVb to Vb of the periodic table, and being different from the polyatom.

6. The catalyst for producing an epoxy compound according to claim 5, wherein said heteropolyoxometalate anion having two defective and/or three defective structure sites is a Keggin-structure heteropolyoxometalate anion.

7. A method of producing an epoxy compound by oxidizing a compound having at least one ethylenic double bond with an oxidizing agent, wherein said method of producing the epoxy compound comprises using the catalyst according to claim 6.

8. A method of producing an epoxy compound by oxidizing a compound having at least one ethylenic double bond with an oxidizing agent, wherein said method of producing the epoxy compound comprises using the catalyst according to claim 5.

9. A catalyst for producing an epoxy compound by oxidizing a compound having at least one ethylenic double bond with an oxidizing agent, which comprises a heteropolyoxometalate anion (A3) containing phosphorus as a heteroatom and tungsten as a polyatom and having two defective and/or three defective structure sites, and an element (E3) being at least one element selected from the group consisting of elements of the fourth to sixth periods of group Va.

10. The catalyst for producing an epoxy compound according to claim 9, wherein said heteropolyoxometalate anion having two defective and/or three defective structure sites is a Keggin-structure heteropolyoxometalate anion.

11. A method of producing an epoxy compound by oxidizing a compound having at least one ethylenic double bond with an oxidizing agent, wherein said method of producing the epoxy compound comprises using the catalyst according to claim 10.

12. A method of producing an epoxy compound by oxidizing a compound having at least one ethylenic double bond with an oxidizing agent, wherein said method of producing the epoxy compound comprises using the catalyst according to claim 9.

* * * * *

UNITED STATES PATENT AND TRADEMARK OFFICE
CERTIFICATE OF CORRECTION

PATENT NO. : 6,743,748 B2
DATED : June 1, 2004
INVENTOR(S) : Noritaka Mizuno et al.

It is certified that error appears in the above-identified patent and that said Letters Patent is hereby corrected as shown below:

Column 27,
Line 60, delete "is" and insert -- being --;

Signed and Sealed this

Twenty-second Day of March, 2005

JON W. DUDAS
*Director of the United States Patent and Trademark Office*